(12) United States Patent
Brown et al.

(10) Patent No.: US 6,306,401 B1
(45) Date of Patent: Oct. 23, 2001

(54) GENETICALLY-ENGINEERED SINDBIS VIRUS WITH MODIFIED E2 GLYCOPROTEIN AND ALTERED HOST-RANGE PHENOTYPE

(76) Inventors: Dennis T. Brown; Racquel Hernandez, both of 3126 Eton Rd., Raleigh, NC (US) 27695

( * ) Notice: Subject to any disclaimer, the term of this patent is extended or adjusted under 35 U.S.C. 154(b) by 0 days.

(21) Appl. No.: 09/157,270

(22) Filed: Sep. 18, 1998

Related U.S. Application Data

(60) Provisional application No. 60/059,668, filed on Sep. 18, 1997.

(51) Int. Cl.[7] .................................................. A61K 39/12
(52) U.S. Cl. ...................................... 424/218.1; 435/320.1
(58) Field of Search ............................... 435/69.1, 320.1; 424/186.1, 218.1

Primary Examiner—Laurie Scheiner
Assistant Examiner—Jeffrey S. Parkin

(57) ABSTRACT

The vaccines and methods of the present invention are based on deletion mutations in the protein transmembrane domains of membrane-enveloped viruses. The strategy for production of these mutations is based on the fact that unlike mammalian cell membranes, the membranes of insect cells contain no cholesterol; thus are thinner than mammalian membranes. Many membrane-coated viruses have membrane glycoproteins on their surface which are responsible for identifying and infecting target cells. These membrane glycoproteins have hydrophobic membrane-spanning domains which anchor the proteins in the membrane bilayer. The membrane-spanning domains of these transmembrane proteins must be long enough to reach from one side of the bilayer to the other in order to hold the proteins in the membrane. Provided is a vaccine, a method of producing this vaccine, and a method of using this vaccine, based on the differences between membranes of viruses replicated in invertebrates and membranes of viruses replicated in vertebrates.

5 Claims, 5 Drawing Sheets

FIGURE 4

GENETICALLY-ENGINEERED SINDBIS VIRUS WITH MODIFIED E2 GLYCOPROTEIN AND ALTERED HOST-RANGE PHENOTYPE

This application claims the benefit of Provisional No. 60/059,668 filed Sept. 18, 1997.

BACKGROUND OF THE INVENTION

1. Field of the Invention

The present invention relates generally to virology and disease control. Specifically, the present invention relates to mutated arthropod vectored viruses and their uses as vaccines.

2. Description of the Related Art

Arthropod vectored viruses (Arboviruses) are viral agents which are transmitted in nature by blood sucking insects. Many of these viruses have membrane bilayers with associated integral membrane proteins which make up the protective envelope of the virus particle (Togaviruses) (Schlesinger, S. and M. J. Schlesinger, 1990).

Collectively, the arthropod vectored viruses are second only to malaria as a source of insect-transmitted disease and death in man and animals throughout the world (Berge A. O. 1975). Among these viral agents are Eastern, Western, and Venezuelan Equine Encephalitis Viruses, Dengue Fever, Japanese Encephalititis, San Angelo Fever, and Yellow Fever. Further, diseases caused by these agents are in resurgence in North America (NIAID *Report of the Task Force on Microbiology and Infectious Diseases* 1992, NIH Publication No. 92-3320) as a result of the introduction of the mosquito vector *Aedes albopictus* (Sprenger, and Wuithiranyagool 1985).

By their very nature, Arboviruses must be able to replicate in the tissues of both the invertebrate insect and the mammalian host (Brown, D. T., and L. Condreay, 1986, Bowers et al. 1995). Differences in the genetic and biochemical environment of these two host cell systems provide a basis for the production of viruses which can replicate in one host but not the other (Host Range Mutants).

Currently, Dengue Fever and Eastern Equine Encephalitis and other insect bourne viruses are in resurgence in the United States. The U.S. Army and other government agencies have been trying to make vaccines against these viruses since the 1960s with little success. Thus, the prior art is deficient in a vaccine against most arthropod vectored viruses and other membrane-coated viruses. The present invention fulfills this long-standing need and desire in the art.

SUMMARY OF THE INVENTION

One object of the present invention is to provide a genetically-engineered, membrane-enveloped virus, wherein the virus codes for a transmembrane protein which has a deletion of one or more amino acids such that the transmembrane protein is able to span the viral membrane when the engineered virus replicates in insect cells, but is unable to span the viral membrane when the virus replicates in mammalian cells. One embodiment of this object of the invention provides an Arthropod vectoral virus as the genetically-engineered, membrane-enveloped virus. Further, in preferred embodiments, the Arthropod vectoral virus may be selected from the group of Togaviruses, Flaviviruses and Bunya viruses and all other enveloped viruses which can replicate naturally in both mammalian and insect cells, as well as enveloped viruses which can be made to replicate in mammalian and insect cells by genetic engineering of either the virus or the cell.

In another embodiment of the present invention, there is provided a method of producing a viral vaccine from a genetically-engineered, membrane-bound virus for vaccination of mammals, comprising the steps of: engineering an amino acid deletion in a viral transmembrane protein to produce an engineered virus, wherein the transmembrane protein is able to span the membrane envelope when the engineered virus replicates in insect cells, but is unable to span the membrane envelope when the virus replicates in mammalian cells, and wherein the virus remains capable of replicating in insect cells; introducing the mutated virus into insect cells; and allowing the mutated virus to replicate in the insect cells to produce a viral vaccine.

In yet another embodiment of the present invention, there is provided a method for vaccination of an individual comprising the steps of: introducing the viral vaccine of the present invention into mammalian cells resulting in the non-productive infection of cells and tissues for immune surveillance.

Finally, the present invention also has the objective of providing a method of producing a viral vaccine from a genetically-engineered, membrane-bound virus to diseases spread by a wild mosquito population to mammals, comprising the steps of: engineering an amino acid deletion in a viral transmembrane protein to produce an engineered virus, wherein the transmembrane protein is able to span the membrane envelope when the engineered virus replicates in mosquito cells, but is unable to span the membrane envelope when the virus replicates in mammalian cells, and wherein the virus remains capable of replicating in wild mosquito cells; introducing the mutated virus into the wild mosquito population; and allowing the mutated virus to replicate in cells of the wild mosquito population to produce a population of mosquitos which harbor the vaccine strain of the virus and exclude the wild type (pathogenic) virus such that the mosquito bite delivers the vaccine to a mammal bitten.

Other and further aspects, features, and advantages of the present invention will be apparent from the following description of one of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 4 shows the deleted amino acids in the $E_2$ transmembranal domain. The deleted sequence is shown under the appropriate amino acid, ranging from 1 deletion to 16. Histidine and Proline sequences beginning at nt. 9787 are on the lumenal side of the protein but are used to design the mutagenic primers.

DETAILED DESCRIPTION OF THE INVENTION

Figure 1:
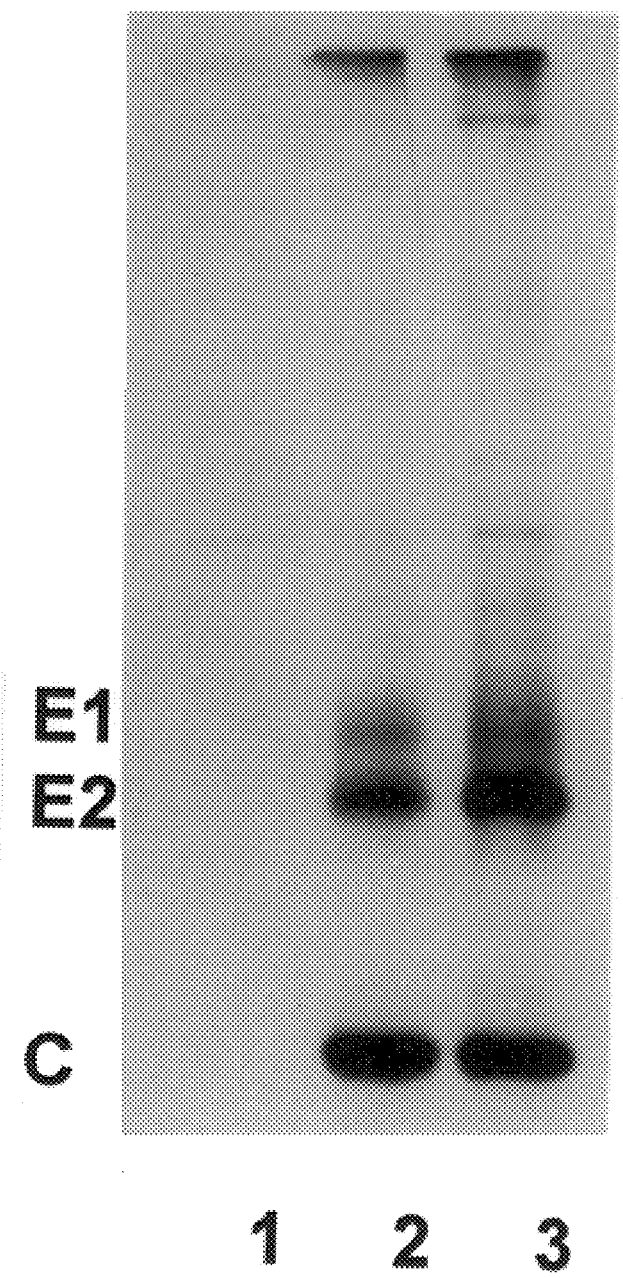
FIG. 1 shows the results of radiolabeled Sindbis virus proteins recovered from transfected tissue-cultured cells. BHK-21 cells mock transfected (1), transfected with mutant Δ391 RNA (2), and *Aedes albopictus* cells transfected with Δ391 RNA (3), were labeled with radioactive amino acids as described in Example 3. At 24 hours post-transfection, proteins were precipitated with virus specific anti-serum as described in Example 4. The figure shows that both BHK-21 cells and *Aedes albopictus* cells transfected with RNA of the deletion mutant produce the three viral structural proteins E1, E2, and C which are not detected in the mock transfected cells.

It will be apparent to one skilled in the art that various substitutions and modifications may be made to the invention disclosed herein without departing from the scope and spirit of the invention.

As used herein, the term "membrane-bound virus" refers to a virus which contains a lipid membrane bilayer as part of its protective exterior coat.

As used herein the term "viral envelope" refers to the lipid membrane component of the membrane containing virus and its associated proteins.

As used herein, the terms "arthropod vectored virus" or "Arbovirus" refer to viral agents which replicate and produce progeny virus in arthropod (insect) or mammalian cells. This includes Togaviruses, Flaviviruses and Bunyaviruses.

As used herein, the term "Togavirus" refers to a general classification of membrane containing viruses which include the Alphaviruses.

As used herein, the term "membrane bilayer" refers to a structure consisting of opposed amphiphatic phospholipids. The bilayer is organized in cross section from polar head groups to non-polar carbon chains to nonpolar carbon chains to polar head groups.

As used herein, the term "glycoprotein transmembrane region" refers to the amino acid sequence of the region of a membrane-integrated protein which spans the membrane bilayer.

As used herein, the term "viral vaccine" refers to a strain of virus or virus mutant which has the antigenic properties of the virus but cannot produce disease.

As used herein the term "immune surveillance" refers to a process by which blood lymphocytes survey the cells and tissues of a mammal to determine the presence of foreign (virus) proteins and stimulates the production of lymphocytes capable of targeting cells producing the foreign protein for destruction. This process also leads to the production of circulating antibodies against the foreign protein.

As used herein, the term "infectious virus particles" refers to viruses which are capable of entering a cell and producing virus protein, whether or not they are capable of producing progeny virus.

As used herein, the term "non-infectious virus particles" refers to viruses which are not capable of infecting or entering a cell.

As used herein, the term "vertebrate cells" refers to any mammalian cell.

As used herein, the term "invertebrate cells" refers to any insect cell.

The present invention is directed to a genetically-engineered, membrane-enveloped virus, wherein the virus codes for a transmembrane protein which has a deletion of one or more amino acids in the transmembrane protein such that the transmembrane protein is able to span the viral membrane when the engineered virus replicates in insect cells, but is unable to span the viral membrane when the virus replicates in mammalian cells. One embodiment of this object of the invention provides an Arthropod vectoral virus selected from the group of Togaviruses, Flaviviruses and Bunya viruses and all other enveloped viruses which can replicate naturally in both mammalian and insect cells, as well as enveloped viruses which can be made to replicate in mammalian and insect cells by genetic engineering of either the virus or the cell.

The present invention is drawn also to a method of producing a viral vaccine from a genetically-engineered, membrane-bound virus for vaccination of mammals, comprising the steps of: engineering an amino acid deletion in a viral transmembrane protein to produce an engineered virus, wherein the transmembrane protein is able to span the membrane envelope when the engineered virus replicates in insect cells, but is unable to span the membrane envelope when the virus replicates in mammalian cells, and wherein the virus remains capable of replicating in insect cells; introducing the mutated virus into insect cells, resulting in the production of mutated virus which can serve as a vaccine.

In addition, the present invention provides a method for vaccination of an individual, comprising the steps of: introducing the viral vaccine of the present invention into cells of an individual; and allowing the vaccine to produce viral proteins for immune surveillance in the individual.

Further, the present invention provides a method of producing a viral vaccine to diseases spread by a wild mosquito population, comprising the steps of: genetically engineering an amino acid deletion in a viral transmembrane protein to produce an engineered virus, wherein said transmembrane protein is able to span said membrane envelope when said engineered virus replicates in mosquito cells, but is unable to span said membrane envelope when said virus replicates in mammalian cells, and wherein the virus remains capable of replicating in mosquito cells; introducing the mutated virus into the wild mosquito population; and allowing the mutated virus to replicate in cells of the wild mosquito population to produce a population of mosquitos which harbor the vaccine strain of the virus and exclude the wild type (pathogenic) virus such that the mosquito bite delivers the vaccine to a mammal bitten.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells And Enzymes" (IRL Press, (1986)); B. Perbal, "A Practical Guide To Molecular Cloning" (1984).

Therefore, if appearing herein, the following terms shall have the definitions set out below.

A "vector" is a replicon, such as plasmid, phage or cosmid, to which another DNA segment may be attached so as to bring about the replication of the attached segment. A vector is said to be "pharmacologically acceptable" if its administration can be tolerated by a recipient animal. Such an agent is said to be administered in a "therapeutically effective amount" if the amount administered is physiologically significant. An agent is physiologically significant if its presence results in a change in the physiology of a recipient mammal. For example, in the treatment of viral infection, a compound which decreases the extent of infection or of physiologic damage due to infection, would be considered therapeutically effective.

A "DNA molecule" refers to the polymeric form of deoxyribonucleotides (adenine, guanine, thymine, or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Various promoters may be used to drive vectors.

The term "oligonucleotide" or "probe" as used herein, refers to a molecule comprised of ribonucleotides or deoxyribonucleotides. The exact size of the oligonucleotide or probe will depend upon many factors which, in turn, depend upon the ultimate function and use of the oligonucleotide. The length of the probe is not critical, but will usually comprise at least about 12 bases, more usually comprising at least about 16 bases, and the probe is substantially complementary to a portion of the bacterial genome; however, the probe need not have perfect complementarity with the genome. The probes may be prepared synthetically, with suitable synthetic techniques, and most likely include a detectable label. Usually, the synthetic sequences are expanded in common, publicly-available cloning vectors and suitable hosts in order to obtain large quantities of the probe. The expanded vectors may themselves be labeled for use as probes, or shorter fragments containing complementary strands may be excised and labeled. Methods for the preparation and utilization of nucleotide probes for diagnostic testing are described in the references listed above, supra, and in U.S. Pat. No. 4,358,535 to Falkow, et al.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, the source of primer and the method used. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transfected" by exogenous or heterologous DNA when such DNA has been introduced inside the cell. The transfecting DNA may or may not be integrated (covalently linked) into the genome of the cell. A "clone" is a population of cells derived from a single cell or common ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene).

It is contemplated that pharmaceutical compositions may be prepared using the novel mutated viruses of the present invention. In such a case, the pharmaceutical composition comprises the novel virus of the present invention and a pharmaceutically acceptable carrier. A person having ordinary skill in this art readily would be able to determine, without undue experimentation, the appropriate dosages and routes of administration of this viral vaccination compound. When used in vivo for therapy, the vaccine of the present invention is administered to the patient or an animal in therapeutically effective amounts, i.e., amounts that immunize the individual being treated from the disease associated with the particular virus. It will normally be administered parenterally, preferably intravenously, but other routes of administration will be used as appropriate. The amount of vaccine administered will typically be in the range of about $10^3$ to about $10^6$ pfu/kg of patient weight. The schedule will be continued to optimize effectiveness while balancing negative effects of treatment. See Remington's Pharmaceutical Science, 17th Ed. (1990) Mark Publishing Co., Easton, Pa.; and *Goodman and Gilman's: The Pharmacological Basis of Therapeutics* 8th Ed (1990) Pergamon Press; which are incorporated herein by reference. For parenteral administration, the vaccine will be most typically formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin.

The vaccines of the present invention are based on deletion mutations in the transmembrane domains of proteins of membrane-enveloped viruses. The strategy for production of these mutations is based on the following information: Unlike mammalian cell membranes, the membranes of insect cells contain no cholesterol (Clayton 1964, Mitsuhashi et al 1983). The presence of cholesterol in membranes in general makes the membrane thicker, with the increase in thickness increasing as the amount of cholesterol increases (Bretscher, 1993). Many membrane-coated viruses have membrane glycoproteins on their surface which are responsible for identifying and infecting target cells (Schlesinger, S. and M. J. Schlesinger, 1990). These membrane glycoproteins have hydrophobic membrane-spanning domains which anchor the proteins in the membrane bilayer (Rice et al 1982).

The membrane-spanning domains of these transmembrane proteins must be long enough to reach from one side of the bilayer to the other in order to hold or anchor the proteins in the membrane. Experiments have shown that if the domains are shortened by the deletion of amino acids within the domain, the proteins do not appropriately associate with the membrane and fall out (Adams and Rose. 1985).

Because insects have no cholesterol in their membranes, the insect-generated viral membrane will be thinner in cross section than the viral membranes generated from mammals. Since the membranes of insects are thinner, the membrane-spanning domains of proteins integrated into insect membranes do not need to be as long as those integrated into the membranes of mammals. It is possible, therefore, to produce deletions in engineered viruses which remove amino acids from the transmembrane domain of the viral glycoprotein. This results in a glycoprotein which can integrate normally into the membrane of a virus replication in an insect cell, but not into the membrane of a virus replicating in a mammal. Thus, the mutated virus is produced in the insect cell replicating as well as the parent, wildtype virus in the insect host. On the other hand, in mammals, the mutant virus can infect the host producing viral proteins; however because the mutated virus glycoprotein cannot span and be anchored in the mammalian membrane, progeny virus cannot be produced in mammalian cells. An additional advantage to the approach of the present invention is that the mutants are engineered as deletion mutants, hence there is absolutely no chance for reversion to wildtype phenotype, a common problem with virus vaccines.

The vaccines envisioned by the present invention work for any membrane-enveloped viruses which grow in vertebrate and invertebrate cells. Indeed, the present invention is applicable to membrane-enveloped viruses which can be either engineered to grow in an insect cell, or to membrane-enveloped viruses which grow in genetically-modified insect cells.

The following examples are given for the purpose of illustrating various embodiments of the invention and are not meant to limit the present invention in any fashion:

EXAMPLE 1
Site-Directed Mutagenesis of Toto 1101

Using the full length clone of the Alpha virus Sindbis described previously (Liu et al 1996, Rice et al., 1987), a deletion removing 3 bases encoding a lysine at position 391 in the amino acid sequence of the virus glycoprotein E2 has been constructed. This lysine is part of the putative membrane-spanning domain of this protein (Rice et al 1982).

Site-directed mutagenesis was used to generate a deletion mutant (Lys391) in Toto 1101, a plasmid containing the full-length Sindbis cDNA and an SP6 promoter that can be used to transcribe infectious RNA from the clone in vitro (Rice et al., 1987 Liu and Brown, 1993a). Using the megaprimer method of PCR mutagenisis (Sarkar and Sommer, 1990) described previously (Liu and Brown, 1993a), three nucleotides were removed in the cDNA clone of Toto 1101, nucleotides (nts) 9801, 9802, 9803, resulting in the removal of the codon AAA (K391).

A 30 base oligonucleotide of the sequence, 5'CTCACG-GCGCGCACAGGCACATAACACTGC3' (SEQ ID No.: 1) was used as the mutagenesis primer. This primer, along with the "forward primer" 5'CCATCAAGCAGTGCGTCG3' (SEQ ID No.: 2; 18mer), generated a 518 base "Megaprimer" (nucleotides 9295–9813). The second PCR reaction consisted of 0.5 µg of megaprimer, 100 µg Toto 1101 template and 0.5 µg of the "reverse primer" 5' GGCAGTGTGCACCTTAATCGCCTGC 3' (SEQ ID No.: 3). All PCR reactions employed 30 cycles at 95 degrees for 1 min., 64 degrees for 1 min., 72 degrees for 1 min. and a final incubation at 72 degrees for 8 min. The resulting PCR product (1149 nts) was cleaved with BCL I and SPL and inserted into the corresponding site in Toto 1101, creating the deletion mutant K391. After the deletion was confirmed by dideoxynucleotide sequencing through the entire subcloned region using Sequenase™ (U.S. Biochemical, Cleveland, Ohio), infectious RNA was transcribed in vitro using SP6 polymerase and was introduced (transfected) into BHK-21 cells.

EXAMPLE 2
In Vitro Transcription and RNA Transfection

Plasmid DNA containing the full-length cDNA copy of Sindbis virus K391 or wild type RNA was linearized with XhoI and transcribed in vitro with SP6 RNA polymerase as described previously (Rice et. al., 1987). 1 µg of Xho I linearized K391 cDNA or wild type Sindbis virus cDNA was transcribed in buffer consisting of 80 mM Hepes pH 7.5, 12 mM MgCl, 10 mM DTT and 2 mM spermidine and 100 µgm BSA with 3 mM each ATP, UTP, CTP, 1.5 mM GTP and 4.5 mM $m^7$ GpppG, 20 units SP6 RNA polymerase and 20 units RNase inhibitor in a 20 µl reaction volume. After incubation at 37° C. for 2 hours, RNA production was assayed by running 2 µl of the RNA product on a 1% agarose gel.

Baby Hamster Kidney (BHK21) cells and *Aedes albopictus* (mosquito) cells were transfected with RNA derived from the mutant or wild type clone. Mosquito cell transfections were carried out using $5×10^6$ cells resuspended in electroporation buffer consisting of 20 mM Hepes pH 7.05, 137 mM NaCl, 0.7 mM $Na_2HPO_4$ and 6 mM dextran. Optimal electroporation parameters for these cells was found to be 2Kv 25µF, Ī resistence. Transfected cells were incubated at 37° C. until cytopathic effect was observed (about 24 hours).

After 24 hours of incubation, the media was collected from both infected cell lines as well as non-RNA transfected controls. The media from each cell line was tested for the presence of infectious virus by plaque assay (as described by Renz and Brown 1976) on mosquito and BHK-21 cell monolayers (Table 1).

TABLE I

Infectious virus produced by transfection of BHK21 or *Aedes albopictus* cells with Sindbis virus wild type or mutant K391

| Cell line Transfected | BHK Mock[a] Transfected | BHK with Wild Type RNA | BHK with K391 RNA | AA Mock Transfected | AA with Wild Type RNA | AA with K391 RNA |
|---|---|---|---|---|---|---|
| Media titered on BHK | no virus detected | $5 × 10^7$ infectious virus/ml | no virus detected | no virus detected | $2 × 10^7$ infectious virus/ml | no virus detected |
| Media titered on AA | no virus detected | $8 × 10^7$ infectious virus/ml | no virus detected | no virus detected | $4 × 10^7$ infectious virus/ml | $1 × 10^7$ infectious virus/ml |

[a]Mock indicates that transfection protocol was carried out without RNA

As shown in Table 1, the mutant K391 produces infectious virus particles only when replicating in the insect cell. This virus, in turn, produced plaques only in mosquito cells. BHK cells transfected with K391 produced no virus detectable when assays were done in either BHK or *Aedes albopictus* cells. If cultures of BHK were infected with the virus produced from the transfected mosquito cells, no detectable virus was produced. RNA encoding wild type virus produced infectious virus which, in turn, produced plaques in both cell lines (Table 1).

EXAMPLE 3
Metabolic Radioactive Labeling of Viral Proteins

Subconfluent monolayers of BHK21 cells in 25 $cm^2$ flasks were transfected with wild type or K391 mutant RNA as described above. Monolayers were starved for 30 min in methionine- and cysteine-free medium (MEM-E) containing 1% FCS, 2 mM glutamine and 5% TPB (starvation medium). At 16 hours post-transfection, cells were pulse-labeled with starvation medium containing 50 µCi/ml [$^{35}$S] Met/Cys protein labeling mix for 20 minutes. Labeling was terminated by washing the monolayers with PBS containing 75 µg/ml cycloheximide. Monolayers were chased for 45 minutes in medium containing 10 times the normal concentration of methionine and cysteine and 75 µg/ml cycloheximide.

EXAMPLE 4
Immunoprecipitation and Polyacrylamide Gel Electrophoresis

Radiolabeled viral proteins were immunoprecipitated with antisera as described (Knipfer and Brown, 1989). [$^{35}$S] Met/Cys labeled cells were washed twice in cold PBS and lysed in lysis buffer: 0.5% NP-40, 0.02 M Tris HCl pH 7.4, 0.05 M NaCl, 0.2 mM PMSF, 0.2 mM TPCK and 0.02 mM TLCK The nuclei were pelleted by centrifugation and discarded. The supernatant was pre-absorbed with 100 µl of protein A/Sepharose beads (Sigma) suspended in lysis buffer for 1 hr, and the beads were pelleted. The pre-absorbed supernatant was treated with 200 µl of protein A/Sepharose beads coupled to rabbit anti-SVHR serum or E2 tail monospecific polyclonal serum and agitated overnight at 4° C. The immunoprecipitated bead-antibody-protein complexes were washed three times with lysis buffer and then solubilized in SDS-PAGE sample buffer consisting of 12% glycerol, 4% SDS, 50 mM Tris pH 6.8, 5% mercaptoethanol and 0.02% bromphenol blue. The samples were heated for 3 min at 95° C. and the beads were removed from the sample by centrifugation. Gel electrophoresis was carried out on a 10.8% SDS-PAGE or 16% Tricine gel as described previously (Liu and Brown, 1993 a,b). Fluorography was performed as described (Bonner and Laskey, 1974) and dried gels were exposed to Kodak XAR-5 film (see FIG. 1).

EXAMPLE 5
Transmission Electron Microscopy

BHK-21 cell monolayers infected with K391 produced from transfected mosquito cells or transfected with K391 RNA were lifted from flasks by trypsin treatment at desired time points, and the cells were pelleted by low speed centrifugation. Cell pellets were washed twice in PBS and fixed in 4% glutaraldehyde at 4° C. overnight. The cells were then washed three times with 0.2 M cacodylate buffer (pH 7.2), post-fixed with 2% osmium tetroxide for 1 hour at room temperature, and washed three times in cacodylate buffer. The cells were stained en bloc for 1 hr at room temperature with 0.5% uranyl acetate. After three washes, cell pellets were embedded in 1% agarose and dehydrated through a graded ethanol/acetone series. Final embedding was in Mollenhauer's (1964) Epon-Araldite epoxy mixture #1 at 70° C. for two days. Ultrathin sections were cut on a Sorvall MT5000 microtome and collected on 150 mesh copper grids. Sections were stained with 1% uranyl acetate and/or lead citrate and were photographed in a Jeol 100CX transmission electron microscope (see FIG. 2).

Figure 2A:
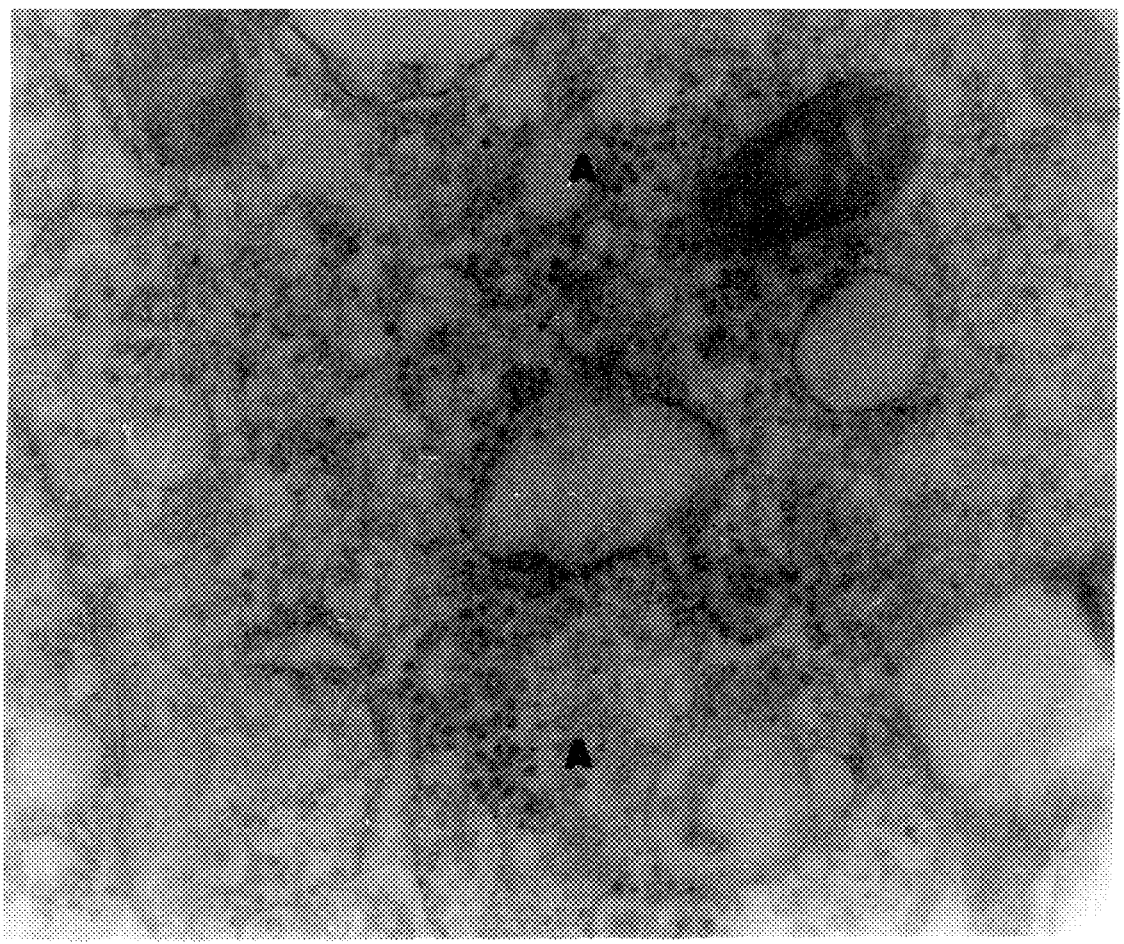
FIGS. 2*a* and 2*b* are electron micrographs of BHK-21 cells (2a) and *Aedes albopictus* cells (2b) transfected with RNA of the Sindbis virus deletion mutant Δ391. Cells were transfected as described in Example 2. BHK-21 cells (a) show clusters of virus core structures in the cell cytoplasm (A) even though these cells produce no mature virus (Table 1). Aedes albopictus cells (b) also produce clusters of virus cores; however, these cores are found free in the cells' cytoplasm similar to those in BHK-21 cells (A) and are also found associated with cell membranes (B). This latter case is not found in BHK-21 cells, indicating that the glycoproteins E1 and E2, although present, do not function to bind them.
Figure 2B:
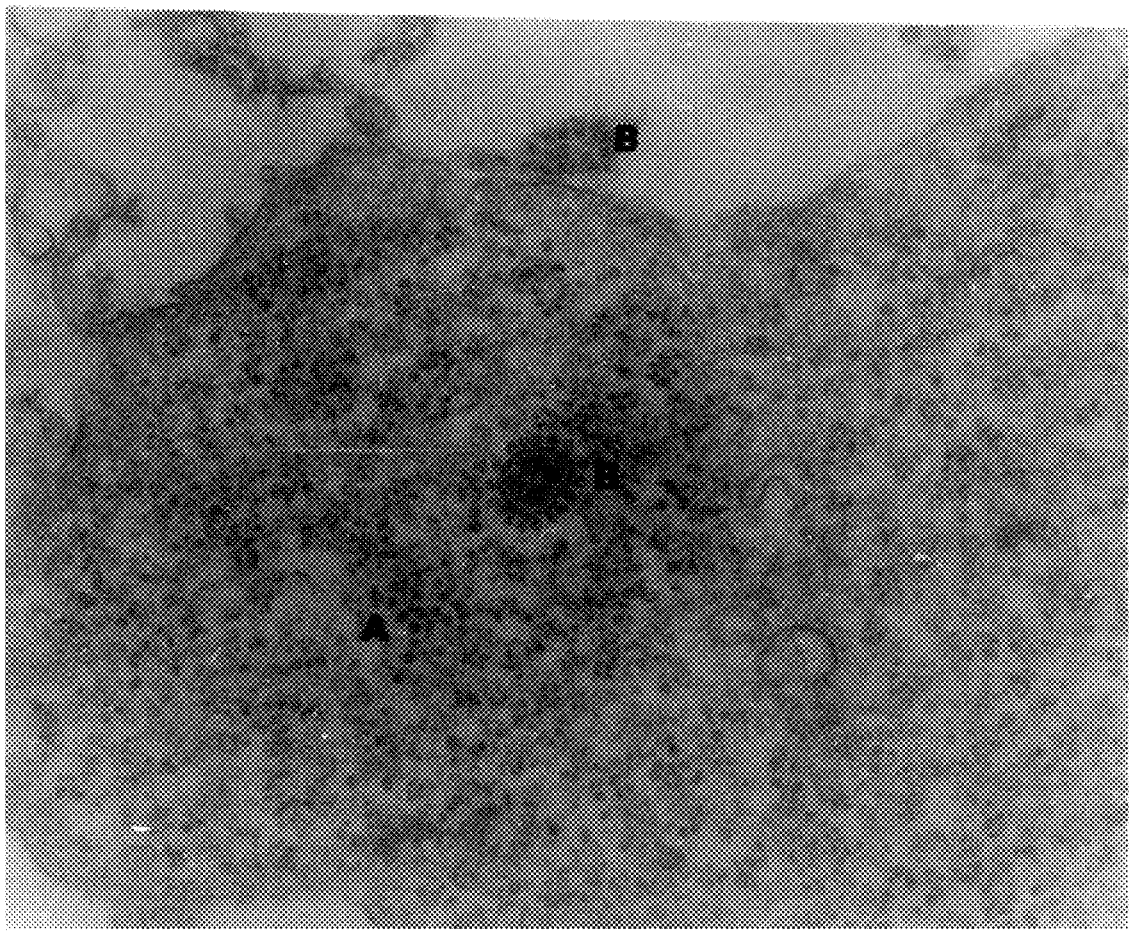

Although BHK cells infected with K391 virus or transfected with K391 RNA produce no virus detectable by the plaque assay, it was shown by PAGE that they do produce all virus structural proteins (FIG. 1). Further, it was shown by electron microscopy that they assemble the intracellular (non infectious) virus cores (FIG. 2).

EXAMPLE 6
Uses for the Sindbis Deletion Mutant K391 and Similar Mutations Produced in Other Togaviruses K391 produces Sindbis virus particles when allowed to replicate in mosquito cells. The exposed regions of the proteins (ecto domains) are wild type in sequence. These wild type proteins allow the virus to enter mammalian cells and produce virus proteins (see FIG. 1) but new virus is not assembled as shown by electron microscopy in FIG. 2.

K391 is a vaccine strain. It is produced in very high concentration in cultured insect cells. However, when the virus is injected into a mammalian host, the virus circulates and infects cells in a mammalian host, these infected cells produce and present virus proteins for immune surveillance, but, because of the truncation in the membrane domain, the infection is limited to those cells infected initially by the innoculum. Because the vaccine strain is the result of a deletion mutation, reversion to wild type pathogenic phenotype is not possible.

Further, an engineered deletion mutant may be introduced into the wild mosquito population. It has been shown that these viruses are spread from the female parent to the progeny by a process of transovariol transmission (Leakey 1984). When these mosquitoes bite a vertebrate they will provide an immunizing dose ($10^6$ infectious particles) of the vaccine strain (for example, K391). Karpf and Brown (1997) showed that infection of insect cells by one Alpha virus prevents the cells from being infected by another, even distantly-related alpha virus for an indefinite amount of time (over two years in cell culture, where the life of a mosquito is 28 days). Thus, the presence of the vaccine strain (for example Sindbis K391) will block the spread of other related and pathogenic viruses by these insects.

EXAMPLE 7
Additional Deletion Mutations

Additional deletion mutations in the membrane spanning domain of Sindbis virus glycoprotein E2 were prepared. The protocol for production of these deletion mutations described below. The procedure is described for the model membrane containing virus Sindbis, however, the procedure can be easily applied to any other virus membrane glycoprotein.

Figure 3:
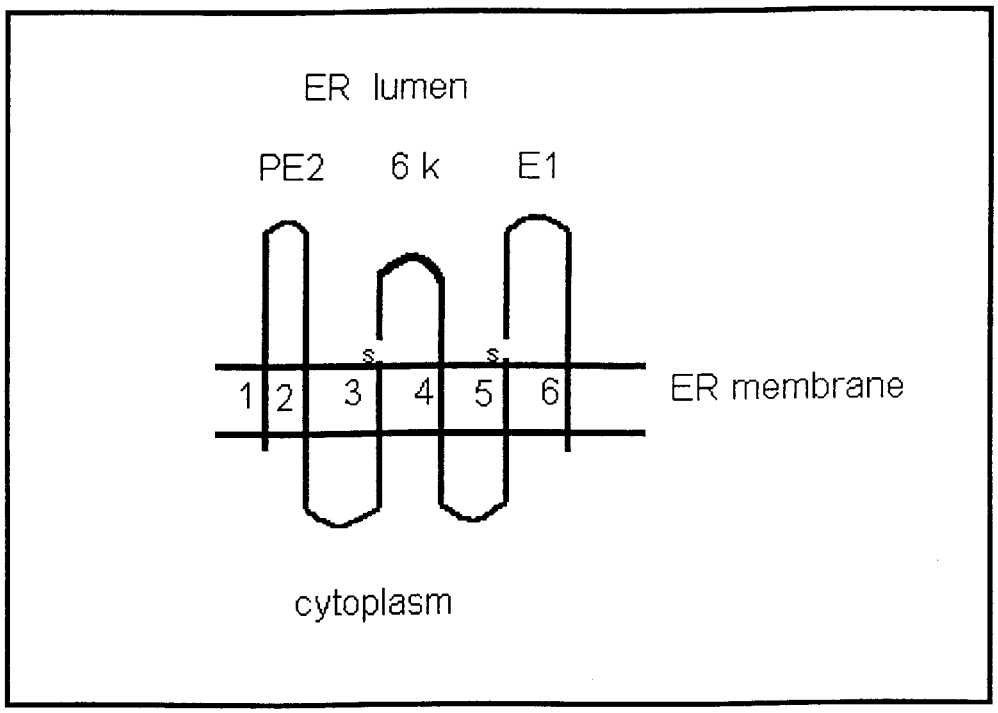
FIG. 3 shows the configuration of Sindbis virus glycoproteins after integration into the ER. The protein is a multipass protein with 6 membrane spanning domains (numbered 1–6). 1. The signal sequence for initial integration. 2. The first E2 trans membrane domain (TMD)). 3. The second E2 TMD. 4. The first 6 k TMD. 5. The second 6k TMD. 6. The E1 TMD. S=point of cleavage by signal peptidase.

The envelope glycoproteins of Sindbis virus were integrated into the membranes of the endoplasmic reticulum as a multi pass protein with 6 membrane spanning domains. There are, therefore, 6 potential targets for the production of deletion mutations which will prevent the correct integration of a transmembrane domain (See FIG. 3). Some of these targets are less satisfactory for this procedure than others. TMD #1 (FIG. 2) is the signal sequence which is recognized by the Signal Recognition Particle and directs protein synthesis to the membranes of the ER. Truncating this domain would likely disturb targeting in both mammalian and insect cells. TMD #3 contains the protein sequence of E2 which recognizes and binds capsid protein. It has been shown that this interaction is very specific in nature and requires the sequence that is in the transmembrane domain (Liu et al., 1996; Lopez et al., 1994). TMD#3, therefore, like TMD#1 has a functional as well as a structural component. A significant deletion in this domain would likely eliminate budding in both cell systems. This leaves four transmembrane domains which are targets for the production of deletions which will effect membrane integration (FIG. 3. TMD 2,4,5,6,).

The 6k protein is not a component of mature virus and its function in virus assembly is not clear. In the poly protein the proper integration and orientation of 6k in the ER membrane is essential for the correct integration of E1. The transmembrane domains of 6k (TMD 4and5) are excellent targets for deletion mutation as failure to integrate one of these domains may cause the poly protein to integrate into the membrane in a wrong configuration or cause the failure to integrate E1. TMD 2 and 6 are the membrane spanning domains of E2 and E1 and are both obvious targets for deletion mutation. Multiple membrane spanning domains in this poly protein suggest that if deletion mutations in a single transmembrane domain do not totally block virus production in mammalian cells, then deletions in additional membrane spanning domains can further reduce maturation to negligible levels.

EXAMPLE 8
Design of Mutagenic Primers for the E2 Hydrophobic Membrane Anchor (TMD#2)

Protocols for testing the requirements placed on the transmembrane domain of E2 (FIG. 3, TMD 2) is given. This protocol can be easily replicated for any other of the Sindbis membrane spanning domains or the membrane spanning domains of any other virus glycoprotein. The hydrophobic Sindbis PE2 membrane anchor consists of 26 amino acids. As is common with other membrane spanning domains little amino acid homology is conserved among the alphaviruses, although the length of this hydrophobic region is highly conserved (Strauss and Strauss, 1994). The lack of sequence conservation in this domain suggests that it is the hydrophobic properties of the domain and not its sequence which is critical for integration.

Figure 4:
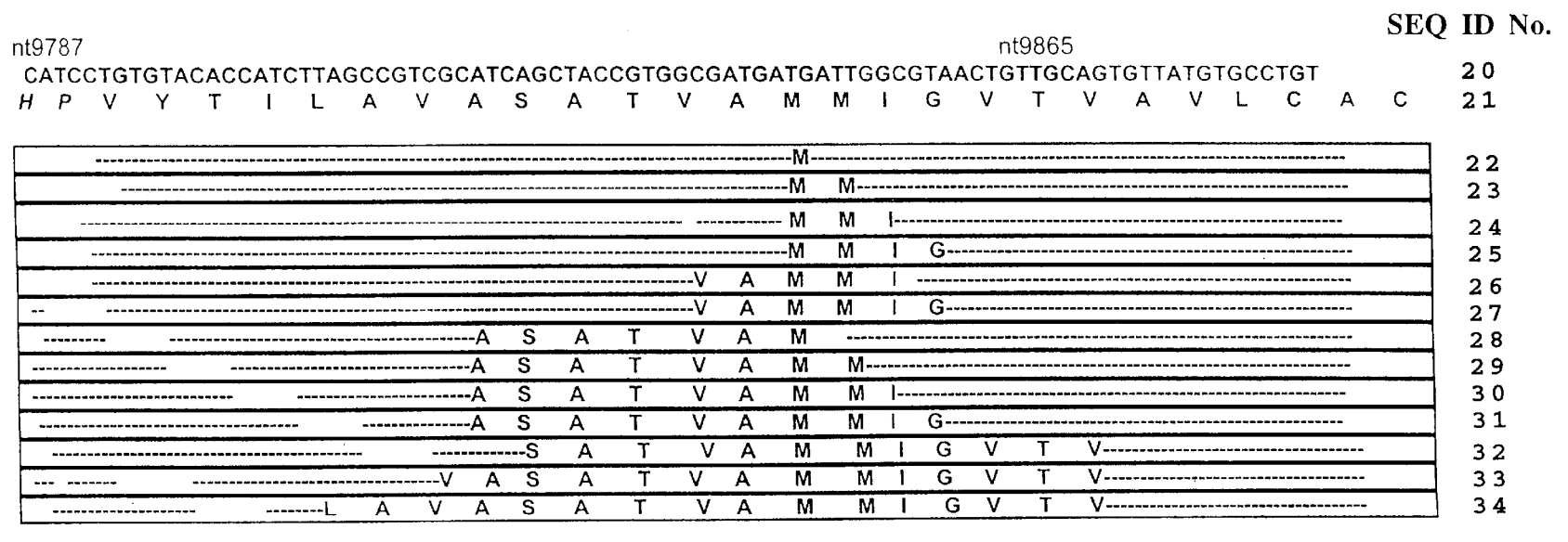

The transmembrane domain of E2 begins at amino acid 365 of the PE2 sequence. This hydrophobic region consists of the sequence: VYTILAVASATVAMMIGVTVAVLCAC (SEQ ID No.: 4). Adams and Rose (1985) demonstrated that a minimum of 14 amino acids in the transmembrane domain of the VSV G protein were necessary for proper anchoring in mammalian cells. Therefore, mutagenic primers have been designed which create a nested set of deletions in the E2 transmembrane domain. Beginning with a deletion of 16 amino acids (which leaves 10 amino acids in the hydrophobic region), a set of deletions were constructed which delete from as many as 16 amino acids, to as few as 1 amino acid from the membrane anchor (FIG. 4).

Deletions were constructed using PCR megaprimer mutagenesis to generate deleted fragments containing unique BclI and SplI sites. All resulting constructs were installed into the w t Sindbis cDNA construct Toto Y420 to generate the mutant plasmids. After linearization with XhoI and transcription using SP6 polymerase, transcripts were transfected into BHK or Aedes albopictus cells by electroporation (as described above). Production of infectious virus from these transfections were titered on both BHK and C710 mosquito cells to determine the host range of these constructs. Table 2 shows the deleted sequences and the primer sequences used in their construction.

For each construct the same primer pair is used to generate the entire BclI to SplI region. The forward primer E1Bcl21 is comprised of the sequence from nucleotide 9306–9327 and reads from $5^1$-$3^1$ GCGTCGCCTATAA-GAGCGACC (SEQ ID No.: 5). The reverse primer Splext is comprised of the sequence from nucleotide 10420–10444 which is the complementary sequence reading from 5¹-3¹ CAGTGTGCACCTTAATCGCCTGC (SEQ ID No.: 6).

The virus produced by transfection of insect cells is tested for its ability to produce plaques in BHK and C7–10 mosquito cells as for the mutant E2 ΔK391. Those mutants which do not produce plaques in BHK cells are tested for their ability to infect BHK cell relative to wild type virus by immunofluorescence assay of infected monolayers. This later assay is compared to the total protein in purified preparations of the mutant and wild type virus to establish the relative infectivity of each mutant population. The goal is to truncate the transmembrane domain as much as possible and still obtain reasonable amounts of virus in C7–10 mosquito cell monolayers which can infect but not produce mature virus in BHK cells. If the circumstance arises that truncation of a single transmembrane domain reduces but does not eliminate virus growth in BHK cells a second domain will be truncated and so fourth up to four domains.

tested for ability to produce immunity in laboratory animals. Those which do produce immunity are candidates for production of human and animal vaccines as is known in the art. This protocol is employed with any arbovirus or other enveloped viruses.

The following references were cited herein:

Adams G. A. and Rose J. K. (1985) Structural requirements of a membrane-spanning domain for protein anchoring and cell surface transport. Cell. 41(3):1007–15

Berge, T. O. (ed.) (1975):*International Catalogue of Arboviruses;* 2nd ed., DHEW Publ. No. (CDC) 75-8301 (U.S. Government Office, Washington, D.C.)

Bonner, W. M., and R. A. Laskey. 1974. A film detection method for tritium-labeled proteins and nucleic acids in polyacrylamide gels. Eur. J. Biochem. 46:83–88.

Bowers, D. F., B. A. Abell and D. T. Brown (1995). Replication and Tissue Tropism of the Alphavirus Sindbis in the Mosquito Aedes Albopictus. Virology 212: 1–12

TABLE 2

Listing of the deletions in Sindbis E2 and the primers used

| PRIMER-DESIGNATED BY NO. OF TRANSMEMBRANAL AMINO ACIDS | NUCLEOTIDES DELETED | OLIGONUCLEOTIDE SEQUENCE OF MUTAGENIC PRIMER (NEGATIVE STRAND) |
|---|---|---|
| E2 TM10 | 9734–9782 | ACATAACACTGCGATGGTGTACAC (SEQ ID No.: 7) |
| E2 TM12 | 9740–9782 | ACATAACACTGCGGCTAAGATGG (SEQ ID No.: 8) |
| E2 TM14 | 9746–9782 | ACATAACACTGCTGCGACGGCT (SEQ ID No.: 9) |
| E2 TM16 | 9743–9773 | GCAACAGTTACGACGGCTAAG (SEQ ID No.: 10) |
| E2 TM17 | 9743–9770 | ACAGTTACGCCGACGGCTAAG (SEQ ID No.: 11) |
| E2 TM18 | 9743–9767 | GTTACGCCAATGACGGCTAAG (SEQ ID No.: 12) |
| E2 TM19 | 9743–9764 | CGCCAATCATGACGGCTAAGA (SEQ ID No.: 13) |
| E2 TM20 | 9755–9773 | GCAACAGTTACGGTAGCTGA (SEQ ID No.: 14) |
| E2 TM21 | 9755–9770 | AGTTACGCCGGTAGCTGA (SEQ ID No.: 15) |
| E2 TM22 | 9761–9773 | TGCAACAGTTACCGCCACGGT (SEQ ID No.: 16) |
| E2 TM23 | 9761–9770 | ACAGTTACGCCCGCCACGGT (SEQ ID No.: 17) |
| E2 TM24 | 9761–9767 | GTTACGCCAATCGCCACGGT (SEQ ID No.: 18) |
| E2 TM25 | 9761–9764 | ACGCCAATCATCGCCACGGT (SEQ ID No.: 19) |

This protocol described by the present invention works for any virus which replicates in insects and mammals and has integral membrane proteins as part of its structure, namely, Togaviruses, Flaviviruses and Bunya viruses and all other enveloped viruses which can replicate naturally in both mammalian and insect cells, as well as enveloped viruses which can be made to replicate in mammalian and insect cells by genetic engineering of either the virus or the cell.

Vaccines are made against any membrane-containing virus by removing amino acids from the membrane-spanning domain of a protein in the viral envelope. This is done by removing bases from a cDNA clone of the virus as described. RNA transcribed from the altered clone is transfected into insect cells. The virus produced is amplified by repeated growth in insect cells until large quantities of mutant virus are obtained. This virus is tested for its ability to infect and produce progeny in mammalian cells. Virus which does not produce progeny in mammalian cells are Bretscher MS. (1993)Cholesterol and the Golgi apparatus. Science. 261(5126):1280 1

Brown, D. T., and L. Condreay (1986). Replication of alphaviruses in mosquito cells. In The Togaviridae and Flaviviridae. S. Schlesinger (ed.), pp. 473–501.

Clayton, R. B. 1964 The utilization of sterols by insects. J. lipid res. 5:3–19

Karpf, et al. (1997) J. Virol. 71:7119–7123.

Knipfer, M. E., and D. T. Brown. 1989. Intracellular transport and processing of Sindbis virus glycoproteins. Virology 170:117–122.

Leake, C. J. (1984). Transovarial transmission of arboviruses by mosquitoes. In Vectors in Virus Biology (Mayo and Harrap, eds.), pp. 63–92. Academic Press.

Liu, N., and D. T. Brown (1993a). Transient translocation of the cytoplasmic (endo) domain of a type-I membrane glycoprotein into cellular membranes. J. Cell Biol. 120:877–883.

Liu, N., and D. T. Brown (1993b). Phosphorylation dephosphorylation events play critical roles in Sindbis virus maturation. J. Virol., 196:703–711.

Liu N., H. Lee, R. Hernandez and D. T. Brown(1996) Mutations in the Endo Domain of Sindbis Glycoprotein E2 Block Phosphorylation, Reorientation of the Endo Domain and Nucleocapsid Binding. Virology 222: 236–246.

Mitsuhashi et al 1983. Sterol free eucaryotic cells from continuous cell lines of insects. Cell Biol. Int. Rep. 7:1057–1062.

Mollenhauer, H. H. 1964. Plastic embedding mixture for use in electron microscopy. Stain Techn. 39:111–114.

NIAID Report of the Task Force on Microbiology and Infectious Diseases (1992). NIH Publication No. 92-3320.

Renz, D., and D. T. Brown. 1976. Characteristics of Sindbis virus temperature-sensitive mutants in cultured BHK-21 and Aedes albopictus (mosquito) cells. J. Virol. 19:775–781.

Rice C. M. et al 1982. Isolation and characterization of the hydrophobic COOH-terminal domains of Sindbis virus glycoproteins. J.Mol.Biol. 154:355–378

Rice., C. M., R. Levis, J. H. Strauss, and H. V. Huang. 1987. Production of infectious RNA transcripts from Sindbis virus cDNA clones: mapping of lethal mutations, rescue of a temperature-sensitive marker, and in vitro mutagenesis to generate defined mutants. J. Virol. 61:3809–3819.

Sarkar, G., and S. S. Sommer. 1990. The "megaprimer" method of site-directed mutagenesis. BioTechniques. 8:404–407.

Schlesinger, S. and M. J. Schlesinger (1990). "Replication of Togaviridae and Flaviviridae." (D. M. Knipe and B. N. Fields, eds.), In Virology Vol. I, pp. 697–711. Raven Press, Ltd., New York.

Sprenger, D. and T. Wuithiranyagool (1985). The discovery and distribution of *Aedes albopictus* in Harris County, TX. J. Am. Mosquito Control Assoc. 2:217–219

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

SEQUENCE LISTING

```
<160> NUMBER OF SEQ ID NOS: 26

<210> SEQ ID NO 1
<211> LENGTH: 205
<212> TYPE: DNA
<213> ORGANISM: Avian leukosis/sarcoma virus of the family Retroviridae
<220> FEATURE:
<223> OTHER INFORMATION: Subgroup A of the avian leukosis/sarcoma virus.

<400> SEQUENCE: 1
ctacagctgt taggttccca gtctctccct aacattacta atattactca gatctccggt      60
gtaaccgggg gatgcgtagg cttcaggcca aaagggttc cttggtatct gggttggtct     120
agacaggaag ccacgcggtt tctccttaga cgcccctctt tctctaactc ctcgaaaccg    180
tttacagtgg tgacagcgga taggc                                            205

<210> SEQ ID NO 2
<211> LENGTH: 229
<212> TYPE: DNA
<213> ORGANISM: Avian leukosis/sarcoma virus of the family Retroviridae
<220> FEATURE:
<223> OTHER INFORMATION: Subgroup B of the avian leukosis/sarcoma virus.

<400> SEQUENCE: 2
ctacaactgc taggttccca gtctctcccc aatataacta atattactcg gatccccagt      60
gtggctggag gatgcatagg ctttacccca tacgatagtc cggctggtgt ctacggatgg    120
gaccggagag aggttacaca catccttctg accgacccag ggaacaatcc tttctttgat    180
aaggcctcta actcctcgaa accgtttaca gtagtgacag cggacaggc                 229

<210> SEQ ID NO 3
<211> LENGTH: 211
<212> TYPE: DNA
```

<213> ORGANISM: Avian leukosis/sarcoma virus of the family Retroviridae
<220> FEATURE:
<223> OTHER INFORMATION: Subgroup C of the avian leukosis/sarcoma virus.

<400> SEQUENCE: 3

| | | |
|---|---|---|
| ctgcagctgc taggttccca gtctctccct aacgttacta acattactca ggtctctggc | 60 |
| gtggccgggg gatgtgtata tttcgcccca agggccactg gcctgttttt aggttggtct | 120 |
| aaacaaggtc tctcgcggtt cctcctccgt caccccttta cctccacctc taactccacg | 180 |
| gaaccgttca cggtggtgac agcggataga c | 211 |

<210> SEQ ID NO 4
<211> LENGTH: 229
<212> TYPE: DNA
<213> ORGANISM: Avian leukosis/sarcoma virus of the family Retroviridae
<220> FEATURE:
<223> OTHER INFORMATION: Subgroup D of the avian leukosis/sarcoma virus.

<400> SEQUENCE: 4

| | | |
|---|---|---|
| ctgcagctgt taggctccca gtctctccct aatatcgcta atattactca gatccctggt | 60 |
| gtggcaggag gatgcatagg cttcacccca tacggcagtc cggctggtgt ttacgggtgg | 120 |
| ggccgggaag aggtgacaca catcctctta accaaccccc ctgataatcc tttctttaac | 180 |
| cgtgcttcta actccacgga accgtttacg gtggtgacag cggataggc | 229 |

<210> SEQ ID NO 5
<211> LENGTH: 228
<212> TYPE: DNA
<213> ORGANISM: Avian leukosis/sarcoma virus of the family Retroviridae
<220> FEATURE:
<223> OTHER INFORMATION: Subgroup E of the avian leukosis/sarcoma virus.

<400> SEQUENCE: 5

| | | |
|---|---|---|
| ctacagctgc taggttccca gtctctccct aacattacta atattactca gatttctggt | 60 |
| gtaaccgggg gatgcgtagg cttcgcccca cactccaatc caagtggtgt ctacgggtgg | 120 |
| ggccggagac aggttacaca caacttcttg atcgccccgt gggtcaatcc tttctttaac | 180 |
| agcgcttcta actccacgga accgttacgg tggtgacagc ggataggc | 228 |

<210> SEQ ID NO 6
<211> LENGTH: 202
<212> TYPE: DNA
<213> ORGANISM: Single Comb White Leghorn chicken
<220> FEATURE:
<223> OTHER INFORMATION: PCR product Fb2, or 2F, isolated from egg
    albumin of ALSV- positive stock F chicken

<400> SEQUENCE: 6

| | | |
|---|---|---|
| acagctgtta ggttcccagt ttttcctcac attattaata ttactcaaat ttctggtgta | 60 |
| accggaggag gcgtaggctt tagaccagga gggatcccct ggtatatagg atggactaga | 120 |
| caggaagcca cacggttcct ccttagacaa tcctcctttt ctaattccac ggaaccattt | 180 |
| acggtggtga cagcggatag gc | 202 |

<210> SEQ ID NO 7
<211> LENGTH: 22
<212> TYPE: DNA
<213> ORGANISM: artificial sequence
<220> FEATURE:
<221> NAME/KEY: primer_bind
<223> OTHER INFORMATION: Forward primer PA1 specific for the detection
    of viral subgroup A of avian/leukosis sarcoma virus.

```
<400> SEQUENCE: 7
ctacagctgt taggttccca gt                                              22

<210> SEQ ID NO 8
<211> LENGTH: 21
<212> TYPE: DNA
<213> ORGANISM: artificial sequence
<220> FEATURE:
<221> NAME/KEY: primer_bind
<223> OTHER INFORMATION: Reverse primer PA2 specific for the detection
      of viral subgroup A of avian/leukosis sarcoma virus.

<400> SEQUENCE: 8
gcctatccgc tgtcaccact g                                               21

<210> SEQ ID NO 9
<211> LENGTH: 202
<212> TYPE: DNA
<213> ORGANISM: Single Comb White Leghorn chicken
<220> FEATURE:
<223> OTHER INFORMATION: RT-PCR product from egg albumin of stock 2F
      chicken.

<400> SEQUENCE: 9
acagctgtta ggttcccagt ttttccctca cattataata ttactcaaat ttctggtgta      60
accggaggag gcgtaggctt tagaccagga gggatcccct ggtatatagg atggactaga     120
caggaagcca cacggttcct ccttagacaa tcctcctttt ctaattccac ggaaccattt     180
acggtggtga cagcggatag gc                                             202

<210> SEQ ID NO 10
<211> LENGTH: 226
<212> TYPE: DNA
<213> ORGANISM: Single Comb White Leghorn chicken
<220> FEATURE:
<223> OTHER INFORMATION: RT-PCR product from egg albumin of stock 6F
      chicken.

<400> SEQUENCE: 10
cagctgttag gttcccagtc tctccctaac attactaata ttactcagat ttctggtgta      60
actgggggat gcgtaggctt caccccacac tccaatccaa gtggtgttta cgggtggggc     120
cggagacagg ttacacacaa cctcttgatc gccccgtggg tcaatccttt ctttaacagc     180
gcttctaact ccacggaacc gtttacggtg gtgacagcgg ataggc                   226

<210> SEQ ID NO 11
<211> LENGTH: 225
<212> TYPE: DNA
<213> ORGANISM: Single Comb White Leghorn chicken
<220> FEATURE:
<223> OTHER INFORMATION: RT-PCR product from egg albumin of stock 7Q
      chicken.

<400> SEQUENCE: 11
cagctgttag gttcccagtt tctccctaac attattaata ttactcagat ttctggtgta      60
actgggggat gcgtaggctt caccccacac tccaatccaa gtggtgttta cgggtggggc     120
cggagacagg ttacacacaa cttcttgatc gccccgtggg tcaatccttt ctttaacagc     180
gcttctaact ccacggaacc gtttacggtg gtgacagcgg atagg                    225

<210> SEQ ID NO 12
<211> LENGTH: 229
<212> TYPE: DNA
```

```
<213> ORGANISM: Single Comb White Leghorn chicken
<220> FEATURE:
<223> OTHER INFORMATION: RT-PCR product from egg albumin of stock 10Q
      chicken.

<400> SEQUENCE: 12
ctacagctgt taggttccca gtctctccct aacattacta atattactca gatttctggt      60
gtaaccgggg gatgcgtagg cttcgcccca cactccaatc caagtggtgt ctacgggtgg     120
ggccggagac aggttacaca caacttcttg atcgccccgt gggtcaatcc tttctttaac    180
agcgcttcta actccacgga accgtttacg gtggtgacag cggataggc                 229

<210> SEQ ID NO 13
<211> LENGTH: 224
<212> TYPE: DNA
<213> ORGANISM: unknown
<220> FEATURE:
<223> OTHER INFORMATION: RT-PCR product from egg albumin of commercial
      chicken from randomly chosen grocery store # 205.

<400> SEQUENCE: 13
gctgttaggt tcccagtctc tccctaacat tactaatatt actcagattt ctggtgtaac    60
cgggggatgc gtaggcttca ccccacactc caatccaagt ggtgtttacg ggtggggccg    120
gagacaggtt acacacaact tcttgatcgc cccgtgggtc aatcctttct taacagcgc    180 ttctaactcc acggaaccgt ttacggtggt gacagcggat aggc                      224

<210> SEQ ID NO 14
<211> LENGTH: 203
<212> TYPE: DNA
<213> ORGANISM: unknown
<220> FEATURE:
<223> OTHER INFORMATION: RT-PCR product from egg albumin of commercial
      chicken from randomly chosen grocery store # 65.

<400> SEQUENCE: 14
tacagctgtt aggttcccag tctctcccta acattactaa catactcaaa tttctggtgt    60
aaccggagga tgcgtaggct ttagaccagg agggatcccc tggtatatgg gatggactag    120
acaggaagcc acacggttcc tccttaaaca atcctccttt tctaattcca cggaaccatt    180
tacggtggtg acagcggata ggc                                             203

<210> SEQ ID NO 15
<211> LENGTH: 21
<212> TYPE: DNA
<213> ORGANISM: artificial sequence
<220> FEATURE:
<221> NAME/KEY: primer_bind
<222> LOCATION: 5564..5585
<223> OTHER INFORMATION: Forward primer PU1 specific for the detection
      of viral subgroup A-E of avian/leukosis sarcoma virus.  Position
      corresponds to the numbering of the RNA genome of the
      Prague C strain of RSV.

<400> SEQUENCE: 15
ctrcarctgy taggytccca g                                               21

<210> SEQ ID NO 16
<211> LENGTH: 21
<212> TYPE: DNA
<213> ORGANISM: artificial sequence
<220> FEATURE:
<221> NAME/KEY: primer_bind
<222> LOCATION: 5772..5791
<223> OTHER INFORMATION: Reverse primer PU2 specific for the detection
```

-continued of viral subgroup A-E of avian/leukosis sarcoma virus.  Position
corresponds to the numbering of the RNA genome of the
Prague C strain of RSV.

<400> SEQUENCE: 16
gycaycactg tcgcctrtcc g                                        21

<210> SEQ ID NO 17
<211> LENGTH: 20
<212> TYPE: DNA
<213> ORGANISM: artificial sequence
<220> FEATURE:
<221> NAME/KEY: primer_bind
<222> LOCATION: 5642..5661
<223> OTHER INFORMATION: Forward primer PA10 specific for the detection
      of viral subgroup A of avian/leukosis sarcoma virus.  Position
      corresponds to the numbering of the RNA genome of the
      Prague C strain of RSV.

<400> SEQUENCE: 17
ggcttcaggc caaaaggggt                                          20

<210> SEQ ID NO 18
<211> LENGTH: 22
<212> TYPE: DNA
<213> ORGANISM: artificial sequence
<220> FEATURE:
<221> NAME/KEY: primer_bind
<222> LOCATION: 5858..5879
<223> OTHER INFORMATION: Reverse primer PA20 specific for the detection
      of viral subgroup A of avian/leukosis sarcoma virus.  Position
      corresponds to the numbering of the RNA genome of the
      Prague C strain of RSV.

<400> SEQUENCE: 18
gtgcattgcc acagcggtac tg                                       22

<210> SEQ ID NO 19
<211> LENGTH: 20
<212> TYPE: DNA
<213> ORGANISM: artificial sequence
<220> FEATURE:
<221> NAME/KEY: primer_bind
<222> LOCATION: 5642..5661
<223> OTHER INFORMATION: Forward primer PB1 specific for the detection
      of viral subgroup A of avian/leukosis sarcoma virus.  Position
      corresponds to the numbering of the RNA genome of the
      Prague C strain of RSV.

<400> SEQUENCE: 19
ggctttaccc catacgatag                                          20

<210> SEQ ID NO 20
<211> LENGTH: 21
<212> TYPE: DNA
<213> ORGANISM: artificial sequence
<220> FEATURE:
<221> NAME/KEY: primer_bind
<222> LOCATION: 5861..5882
<223> OTHER INFORMATION: Reverse primer PB2 specific for the detection
      of viral subgroup A of avian/leukosis sarcoma virus.  Position
      corresponds to the numbering of the RNA genome of the
      Prague C strain of RSV.

<400> SEQUENCE: 20
acacatcctg acagatggac c                                        21

<210> SEQ ID NO 21
<211> LENGTH: 20

```
<212> TYPE: DNA
<213> ORGANISM: artificial sequence
<220> FEATURE:
<221> NAME/KEY: primer_bind
<222> LOCATION: 5642..5661
<223> OTHER INFORMATION: Forward primer PC1 specific for the detection
      of viral subgroup C of avian/leukosis sarcoma virus.  Position
      corresponds to the numbering of the RNA genome of the
      Prague C strain of RSV.

<400> SEQUENCE: 21
tatttcgccc caagggccac                                              20

<210> SEQ ID NO 22
<211> LENGTH: 22
<212> TYPE: DNA
<213> ORGANISM: artificial sequence
<220> FEATURE:
<221> NAME/KEY: primer_bind
<222> LOCATION: 5858..5879
<223> OTHER INFORMATION: Reverse primer PC2 specific for the detection
      of viral subgroup C of avian/leukosis sarcoma virus.  Position
      corresponds to the numbering of the RNA genome of the
      Prague C strain of RSV.

<400> SEQUENCE: 22
ccacgtctcc acagcggtaa gt                                           22

<210> SEQ ID NO 23
<211> LENGTH: 20
<212> TYPE: DNA
<213> ORGANISM: artificial sequence
<220> FEATURE:
<221> NAME/KEY: primer_bind
<222> LOCATION: 5642..5661
<223> OTHER INFORMATION: Forward primer PD1 specific for the detection
      of viral subgroup D of avian/leukosis sarcoma virus.  Position
      corresponds to the numbering of the RNA genome of the
      Prague C strain of RSV.

<400> SEQUENCE: 23
ggcttcaccc catacggcag                                              20

<210> SEQ ID NO 24
<211> LENGTH: 21
<212> TYPE: DNA
<213> ORGANISM: artificial sequence
<220> FEATURE:
<221> NAME/KEY: primer_bind
<222> LOCATION: 5858..5882
<223> OTHER INFORMATION: Reverse primer PD2 specific for the detection
      of viral subgroup D of avian/leukosis sarcoma virus.  Position
      corresponds to the numbering of the RNA genome of the
      Prague C strain of RSV.

<400> SEQUENCE: 24
ccatacgtcc tcacagatag a                                            21

<210> SEQ ID NO 25
<211> LENGTH: 20
<212> TYPE: DNA
<213> ORGANISM: artificial sequence
<220> FEATURE:
<221> NAME/KEY: primer_bind
<222> LOCATION: 5642..5661
<223> OTHER INFORMATION: Forward primer PE1 specific for the detection
      of viral subgroup E of avian/leukosis sarcoma virus.  Position
      corresponds to the numbering of the RNA genome of the
      Prague C strain of RSV.

<400> SEQUENCE: 25
```

```
ggcttcgccc cacactccaa                                               20
```

```
<210> SEQ ID NO 26
<211> LENGTH: 22
<212> TYPE: DNA
<213> ORGANISM: artificial sequence
<220> FEATURE:
<221> NAME/KEY: primer_bind
<222> LOCATION: 5867..5888
<223> OTHER INFORMATION: Reverse primer PE2 specific for the detection
      of viral subgroup E of avian/leukosis sarcoma virus.  Position
      corresponds to the numbering of the RNA genome of the
      Prague C strain of RSV.

<400> SEQUENCE: 26
gcacatctcc acaggtgtaa at                                            22
```

What is claimed is:

1. A genetically-engineered, membrane-enveloped Sindbis virus containing a modified virus membrane glycoprotein E2 and bearing an altered host-range phenotype that enables the virus to replicate efficiently in insect cells, but not mammalian cells, wherein said E2 glycoprotein has been modified by introducing deletions into the membrane spanning domain, said deletions resulting in a modified E2 that is capable of spanning insect cell membranes, but not mammalian cell membranes, and an altered host-range phenotype that enables the virus to infect and produce progeny virus in insect cells, and to infect, but not produce progeny virus, in mammalian cells.

2. The genetically-engineered, virus of claim 1, wherein said insect cells are mosquito cells.

3. The mosquito cells of claim 2, wherein said mosquito cells are *Aedes albopictus* cells.

4. The genetically-engineered virus of claim 1, wherein said mammal is a human.

5. The genetically-engineered virus of claim 1, wherein said virus is Sindbis virus K391 that has a lysine deletion at position 391 of the virus glycoprotein E2.

* * * * *

UNITED STATES PATENT AND TRADEMARK OFFICE
CERTIFICATE OF CORRECTION

PATENT NO.    : 6,306,401 B1
DATED         : October 23, 2001
INVENTOR(S)   : Dennis T. Brown and Racquel Hernandez It is certified that error appears in the above-identified patent and that said Letters Patent is hereby corrected as shown below:

<u>Column 10,</u>
Line 14, please insert a period after "TLCK".

<u>Column 11,</u>
Line 46, please insert the word -- is -- before the word "described".

<u>Column 12,</u>
Line 25, "is" should read -- are --.

<u>Column 13,</u>
Line 7, "cell" should read -- cells --.

<u>Column 15,</u>
Line 23, please remove the period after the word "Rice".

<u>Column 28,</u>
Line 21, please delete the comma after the work "engineered".

Signed and Sealed this

Thirtieth Day of July, 2002

Attest:

JAMES E. ROGAN
*Attesting Officer*   *Director of the United States Patent and Trademark Office*